United States Patent [19]
Grodberg et al.

[11] Patent Number: 4,859,467
[45] Date of Patent: Aug. 22, 1989

[54] SUSTAINED RELEASE FLUORIDE COMPOSITION

[75] Inventors: Marcus G. Grodberg, Newton, Mass.; David J. Baylink, Redlands, Calif.

[73] Assignee: Colgate-Palmolive Company, New York, N.Y.

[21] Appl. No.: 911,608

[22] Filed: Sep. 25, 1986

[51] Int. Cl.⁴ .......................... A61K 9/22; A61K 9/26; A61K 33/16
[52] U.S. Cl. .................................. 424/606; 424/468; 424/469; 424/676
[58] Field of Search .................. 424/52, 151, 468, 469

[56] References Cited
U.S. PATENT DOCUMENTS

| | | | |
|---|---|---|---|
| 2,449,184 | 9/1948 | Strean | 424/52 |
| 2,627,493 | 2/1953 | Merckel et al. | 424/52 |
| 2,967,131 | 1/1961 | Elbreder et al. | 424/151 |
| 3,119,743 | 1/1964 | Ericsson | 424/52 |
| 3,312,594 | 4/1967 | Cyr et al. | 424/151 |
| 3,431,339 | 3/1969 | Gyarmathy et al. | 424/52 |
| 4,169,885 | 10/1979 | Raaf et al. | 424/151 |
| 4,265,877 | 5/1981 | Tenta et al. | 424/151 |
| 4,726,952 | 2/1988 | Walsoorf et al. | 424/151 |
| 4,728,513 | 3/1988 | Ventouras | 424/151 |

FOREIGN PATENT DOCUMENTS

| | | | |
|---|---|---|---|
| 3127984 | 2/1983 | Fed. Rep. of Germany | 424/151 |
| 2497665 | 7/1982 | France | 424/151 |
| 1221633 | 2/1971 | United Kingdom . | |

OTHER PUBLICATIONS

Eisch CA.89:12151a (1978).
Jowsey CA.89:122856s (1978).
Becker GA.90:132993u (1979).
Erickson CA.90: 180340a (1979).
Fuchs CA.91:186370c (1979).
White CA.99:200373e (1983).
Baylink CA.99:205347a (1983).
Anderson CA.104:45750e, 45761f (1986).

Primary Examiner—Shep K. Rose
Attorney, Agent, or Firm—Norman Blumenkopf; Murray M. Grill

[57] ABSTRACT

A medication for providing fluoride ion for the prevention and treatment of bone loss disease. The dosage is a lozenge, tablet or capsule containing from 20 to 100 milligrams of sodium monofluorophosphate and further includes a slow release mechanism for controlling release of the fluoride ion over a period of up to eight hours after swallowing. Up to ten percent of sodium fluoride can be added.

2 Claims, No Drawings

SUSTAINED RELEASE FLUORIDE COMPOSITION

BACKGROUND OF THE INVENTION

1. Field of the Invention

This invention relates to a sustained release systemic fluoride drug product for treatment or prevention of osteoporosis or other bone disease. More particularly, this invention relates to the use of sodium monofluorophosphate, alone or in combination with another fluorine compound, in a sustained release solid unit dosage form, suitable for use in the treatment and prevention of osteoporosis, alveolar bone loss or other bone diseases where systemic fluoride ion is efficacious.

2. Description of the Prior Art

Fluroide stimulates the activity of bone-forming cells and, together with calcium and phosphate, the two major components of bone is also stored in the bone structure. Fluoride seems to directly stemulate the proliferation of osteoblasts resulting in an increase in bone formation.

U.S. Pat. No. 3,287,219 discloses the oral administration of sodium fluoride to promote bone healing.

The role of fluoride in strengthening the teeth and in imparting acid resistance and preventing caries in dental treatment is well documented. The use of sodium fluoride tablets and liquids for infants and young children in areas where the drinking water is not or is only insufficiently fluoridated is well known. For this purpose, fluoride ion from NaF is administered in dosages of about 0.25 to about 1 mg per day. Representative patents in this area include U.S. Pat. Nos. 3,306,824, 4,265,877 and 4,397,837 (toothpaste). The use of sodium monofluorophosate (MFP) in dental products, particularly toothpaste products, as an anticaries fluoride additive is also well known and is mentioned in U.S. Pat. No. 4,397,837 cited above. The MFP is slowly metabolized by an intestinal enzyme, MFPase or alkaline phosphatase into free fluoride ion which, in turn, is absorbed into the blood stream, some of the MFP being directly absorbed in the liver and converted therein to F ion.

More recently, the use of NaF or MFP for the treatmean of bone disease to promote bone formation and strengthen bone has received wide attention. In fact, although not yet approved for use in the United States, both NaF and MFP products for the treatment and prevention of osteoporosis are available in Europe. Thus, Flurexal ® is an enteric coated tablet containing 22 mg sodium fluoride (10 mg F) sold by Zyma SA Nyon Suisse; Tridin ® is a chewable tablet containing 38 mg sodium monofluorophosphate (5 mg F), 500 mg calcium gluconate monohydrate, 500 mg calcium citrate tetrahydrate, 200 mg carboxymethyl cellulose, available from Opfermann Arzneimittel GmbH.

According to the directions for use provided with the medications, Flurexal ® should be taken three times each day, while Tridin ® should be taken 1-2 tablets three times a day for treatment or one tablet three times a day for prevention of steroid-osteoporosis. In general, the typical recommended dosage for F ion is in the order of from about 30 to 60 mg per day for a human adult.

The literature provided with Tridin ® states that gastric and intestinal irritation is seldom observed. To the same effect, Yngve Ercisson, "Monofluorophosphate Physiology: General Considerations," Caries Res. 17 (Suppl. 1), pages 46-55 (1983), reported that "neither in patients nor in numerous experiments with laboratory workers has any subjective discomfort been recorded with doses up to 30 mg F as MFP." However, in one of the present inventors' own clinical studies and patient evaluations, the occurrence of gastric and intestinal distress was observed in a significant number of cases.

Attempts to solve the adverse side effects of gastrointestinal (GI) tract symptoms by minimizing the availability of F ion in the stomach by providing NaF in a sustained release form have only been partially effective in avoiding GI irritation. More particularly, it has been observed that, while slow release sodium fluoride is well tolerated by approximately 70% of patients, there is adverse gastrointestinal effects in the other approximate 30% of patients.

SUMMARY OF THE INVENTION

The present invention provides a fluoride treatment for osteoporosis, alveolar bone disease and other localized bone disorders which virtually solves the problem of gastric irritation.

Quite surprisingly, in view of the fact that the sustained release type unitary dosage product for administering NaF is only variably effective in avoiding the occurrence of gastric irritation, it has now been discovered that, when MFP is administered in a sustained release form, the occurrence of gastric intestinal irritation is almost totally eliminated.

Accordingly, it is an object of this invention to provide a fluoride ion drug preparation useful in the treatment or prevention of osteoporosis (bone disease) which does not cause adverse GI symptoms, such as gastric irritation.

It is a specific object of this invention to provide a unitary dosage form of MFP which provides sufficient quantities of F ion to be useful in the prevention or treatment of osteoporosis in which the MFP is administered from the unitary dosage product at a slow rate over the course of at least several hours, preferably a maximum of eight hours, whereby occurrence of gastric irritation is avoided.

It is another object of the invention to provide a method for treating or preventing osteoporosis by administering, at least once daily, to a patient suffering from or at risk for osteoporosis a solid, unitary dosage product containing sufficient amount of MFP effective for the promotion of, or maintenance of, formation and strengthening or diseased or weakened bone wherein the product includes means for slowly releasing the MFP over the course of at least several hours to a maximum of eight hours.

In accordance with these objectives and other objects, which will become apparent from the following desdription, the present invention provides, in one aspect thereof, a medication for providing fluoride ion for the treatment or prevention of osteoporosis or other bone disease, including alveolar bone loss, which is in the form of a solid unitary dosage tablet or capsule containing from about 20 milligrams (mg) to about 100 mg of sodium monofluorophosphate ($Na_2PO_3F$) and further including means for controlling the release of the monofluorophosphate over a period extending up to a maximum of eight hours whereby the quantity of fluoride ion present in the stomach at any given time is below the threshhold value at which gastric irritation will occur.

The sustained release unitary dosage product of this invention may include MFP as the sole active ingredient. Alternatively, MFP may be used in combination with NaF, or a mixture thereof.

In a specific and preferred embodiment of the invention, the means for controlling release of MFP and any other active ingredient includes a mass of water swellable cellulosic powder forming a coherent fibrous powder network as a matrix in which the monofluorophosphate is uniformly and homogeneously dispersed, whereby, upon introduction of the unitary dosage product into an aqueous medium, the cellulosic fibers at the surface of the product soften and loosen from the remaining mass of fibers to thereby release a stream of the monofluorophosphate.

The initial loosening of the fibers causes a delay in the release of the fluoride ion or a very slow release thereof for the first one to three hours, allowing the dosage to pass through the stomach and into the intestinal tract before the uniform release of the fluoride ion occurs.

According to the method aspect of the invention, a patient suffering from or at risk of osteoporosis is treated with at least one of the sustained release unitary dosage MFP products of this invention along or with a calcium ion supplement.

DETAILED DESCRIPTION OF THE INVENTION

Osteoporosis can be broadly defined as increasing weakness and fragility of the bones. It most frequently occurs in elderly, post-menopausal women and in elderly (presenile or senile) men, but also occurs in idiopathic forms. Osteoporosis can also occur in connection with, i.e. as an undesirable side effect of, corticoid treatment (steroid-osteoporosis). Certain localized forms of bone disease may also be associated with a general weakness and fragility of the bone structure due to insufficient new bone formation. Therapeutic indications includes any bone wasting disease, genetic, such as osteogenesis infection, or acquired, such as renal bone disease.

One of the effects of advanced periodontal disease is the loss of alveolar bone (i.e. that portion of the jaw bones that support the teeth) mass, which eventually causes loosening and loss of teeth. Alveolar bone loss may also occur after tooth extractions and, in some cases, after the insertion of dental implants.

Bone is composed of an organic phase, collogen and an inorganic crystalline phase of calcium phosphate, or more specifically, hydroxyapatit, $Ca_{10}(PO_4)_6(OH)_2$. Fluoride plays an important role in the prevention of bone loss by stimulating the formation of less soluble fluorapatite $Ca_{10}(PO_4)_6F_2$. Therefore, in osteoporosis, alveolar bone loss and other bone diseases associated with general weakening or loss of the bone tissue, or in cases where the normal dietary intake of calcium is insufficient, a dietary supplement to supply additional calcium is usually appropriate. The addition to the calcium supplement of, or the separate administration of, a source of fluoride ion will, according to recent scientific research, greatly enhance the reversal of bone loss, the fluoride stimulating new bone formation and the calcium being an indispensable building block for bone tissue.

Sodium fluoride and sodium monofluorophosphate can each be used to provide the fluoride ion to be adsorbed into the blood for eventual skeletal uptake. Sodium fluoride, NaF, has the advantage that it has a higher F content than sodium monofluorophosphate, MFP. NaF is also more rapidly absorbed, at least in the first few hours, into the blood. However, NaF has higher acute toxicity than MFP and causes stomach irritation in a much higher percentage of patients than does MFP. Moreover, and perhaps most important, is the fact that NaF is incompatible with ionizable calcium compounds, forming insoluble $CaF_2$, thereby depleting the availability of the F ion to a large extent and of the Ca ion to a smaller extent (based on the much greater total quantity of calcium present in the patient's system). On the other hand, MFP is compatible with ionizable calcium compounds since Ca(MFP) is about twenty times more soluble than $CaF_2$.

Unfortunately, when ingested orally in the recommended dosages, typically about 30 to 60 mg F per day for human adults, MFP, although not as pronounced as NaF, also causes stomach irritation.

In accordance with the present invention, it has been found that by incorporating the MFP alone or in combination with a small amount of sodium fluoride, the occurrence of GI irritation can be avoided. Although not wishing to be bound by any particular theory, it is presumed that, by only gradually releasing the MFP from the unitary dosage product, the quantity of fluoride ion present in the stomach at any given time is below the threshhold value at which gastrointestinal irritation will occur. Since a similar alleviation of GI symptoms is not observed for a slow release NaF product, it is further presumed that the more rapid ionization of NaF into sodium and fluorine ions, as compared to the rate of enzymatic hydrolysis of MFP in the stomach, may also account for this different result. In any case, by whatever mode of action, by incorporating the MFP with means for controlling the release of the monofluorophosphate over a period extending up to a maximum of eight hours from the time of ingestion, gastrointestinal irritation will be avoided.

The means for providing controlled (i.e. sustained) release of teh active ingredient may be selected from any of the known sustained-release oral drug delivery systems. Some of the known sustained-release delivery systems for controlling the release of an active ingredient over a course of about four or more hours include the wax matrix system, the coated granular system, the "miniature osmotic pump" system and the Forest Synchron system (of Forest Laboratories).

The wax matrix system disperses the active ingredient(s) in a wax binder which slowly dissolves in body fluids to gradually release the active ingredient(s).

The coated granular system encapsulates the active ingredient(s) in various polymeric coatings that have varying degrees of solubility dependent upon pH and/or enzymes to vary the drug release rate from the respective granules. A multiplicity of granules is filled into a gelatin or similar water-soluble capsule.

In the miniature osmotic "pump," an active ingredient is coated with a semipermeable membrane. The pump works when water-soluble drugs are released through a hole drilled into the membrane.

The preferred controlled-release oral drug delivery system is the Forest Synchron drug delivery system in which the active ingredient, FP, is dispersed uniformly and homogeneously throughout a mass of water-swellable modified cellulosic powder or fibers forming a coherent network, as a matrix. The mixture of the fibrous or powdery mass and active ingredient(s), with optional additives such as flavoring, binder, lubricant, processing aids and the like, is compacted into a table which, prior to use, is hard and dry. After the tablet is swallowed and comes into contact with the aqueous stomach and intestinal fluids, the outer layer of the tablet becomes soft and gelatinous while the inner portions remain dry. At the softened and gelatinous surface, the cellulose powder or fibers become loose and separate from the remaining mass, thereby releasing a portion of the active ingredients. During the period the tablet remains in the stomach and then travels down through the GI tract, the newly exposed outer surfaces become moistened and in turn become soft and gelatinous to loosen additional cellulosic material, thereby allowing additional amounts of MFP and any dispersed substances to be steadily and generally uniformly released into the stomach or intestines. By the time the tablet has passed through the GI tract, after about four to eight hours, the tablet is completely dissipated and dissolved. Accordingly, the ingested tablet will release a stream of the sodium monofluorophosphate as well as any other active ingredient.

For further details and discussion of the Forest Synchron drug delivery systems, reference is made to the following U.S. Patents, the disclosures of which are incorporated hereby by reference thereto: Nos. 3,870,790, 4,226,849, 4,357,469, 4,369,172, and 4,389,393, all assigned to Forest Laboratories, Inc.

A typical formulation of a sustained-release unitary dosage capsule according to the invention which utilizes a coated granular system is shown immediately below:

| Ingredient | Amount (milligrams) |
|---|---|
| Sodium monofluorophosphate | 76.3 |
| Sugar | 158.3 |
| Starch | 40.3 |
| Glucose | 2.0 |
| Food Grade Shellac | 7.8 |
| Talcum powder | 12.6 |
| Ethyl cellulose | 2.3 |
| Castor Oil | 0.4 |
| | Total Content Weight 300 mg |

This formulation provides 10 mg F ion as MFP and is designed to release the MFP in the gastrointestinal tract slowly over a period of up to eight hours after ingestion.

The amount of MFP can generally be varied over a range of from about 20 mg to about 100 mg MFP per tablet (or pill, capsule, etc.) to provide correspondingly from about 2.5 mg to about 13 mg F per tablet. Therefore, based on the current recommended dosage for treatment for osteoporosis and related bone diseases, of from about 30 to 60 mg F per day and recommended dosages of, at most, about one-half these levels for prevention of osteoporosis in, for example, postmenopausal women and presenile or senile men, or for prevention of steroid-osteoporosis or alveolar bone loss, total daily dosages of one or two tablets two or four times a day will provide the total recommended requirement of fluoride.

The use of sodium monofluorophosphate as the sole fluoride source is preferred. However, if desired, the formulation can include small amounts of NaF or other water-soluble fluoride compound. Thus, NaF is amounts up to about ten percent (10%), such as 5 to 10%, by weight based on the total weight of NaF+MFP can be added to a sustained-release medication. It has been found that the administration of NaF unexpectedly increases alkaline phosphatase enzyme levels in the intestines, thereby enhancing the formation of F from MFP.

What is claimed is:

1. A medication for providing fluoride ion for the treatment and prevention of bone loss disease including osteoporosis and alveolar bone loss, which comprises a solid, unitary dosage tablet, containing from about 20 to 100 milligrams of sodium monofluorophosphate and further containing a coherent network matrix of a hard dry compacted mass of water swellable gel-forming fibrous powder means for controlling the release of the monofluorophosphate at a slow rate over a period extending from at least 4 hours up to eight hours after swallowing, whereby the quantity of fluoride ions at any given time is below the threshold value at which gastric irritation will occur, further comprising from 5 to 10% by weight of sodium fluoride based on the combined weight of sodium monofluorophosphate and sodium fluoride.

2. The composition of claim 1, wherein the means for controlling release of the monofluorophosphate comprises a mass of water-swellable cellulosic powder or fiber forming a coherent network as a matrix in which the monofluorophosphate is uniformly and homogeneously dispersed, whereby, upon introduction of the unitary dosage into an aqueous medium, the cellulosic powder or fibers at the surface of the unitary dosage soften and loosen from the remaining mass to thereby release a stream of the monofluorophosphate.

* * * * *